(12) United States Patent
Danley

(10) Patent No.: US 9,964,454 B2
(45) Date of Patent: May 8, 2018

(54) THERMOPILE DIFFERENTIAL SCANNING CALORIMETER SENSOR

(71) Applicant: WATERS TECHNOLOGIES CORPORATION, Milford, MA (US)

(72) Inventor: Robert L. Danley, Milford, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 360 days.

(21) Appl. No.: 14/778,854

(22) PCT Filed: Mar. 20, 2014

(86) PCT No.: PCT/US2014/031288
§ 371 (c)(1),
(2) Date: Sep. 21, 2015

(87) PCT Pub. No.: WO2014/153438
PCT Pub. Date: Sep. 25, 2014

(65) Prior Publication Data
US 2016/0047700 A1 Feb. 18, 2016

Related U.S. Application Data

(60) Provisional application No. 61/804,384, filed on Mar. 22, 2013.

(51) Int. Cl.
*G01K 17/00* (2006.01)
*G01N 25/20* (2006.01)
*G01K 3/08* (2006.01)

(52) U.S. Cl.
CPC ............... *G01K 17/00* (2013.01); *G01K 3/08* (2013.01); *G01N 25/20* (2013.01)

(58) Field of Classification Search
CPC ............... G01N 25/482; G01N 25/486; G01N 25/4853; G01N 25/4866
See application file for complete search history.

(56) References Cited

U.S. PATENT DOCUMENTS 4,251,290 A 2/1981 Gomez
5,033,866 A 7/1991 Kell et al.
(Continued)

FOREIGN PATENT DOCUMENTS

CN 102156148 A 8/2011
CN 102928460 A 2/2013
(Continued)

OTHER PUBLICATIONS

Extended European Search Report dated Sep. 26, 2016 in European Patent Application No. 14768293.4.
(Continued)

*Primary Examiner* — Clayton E LaBalle
*Assistant Examiner* — Leon W Rhodes, Jr.
(74) *Attorney, Agent, or Firm* — Schmeiser, Olsen & Watts LLP

(57) ABSTRACT

A heat flow sensor for a heat flux differential scanning calorimeter comprising twin thermopiles. The thermopiles each comprise positive and negative thermocouple alloys and electrically insulating ceramic components. Diffusion bonding is used to form thermocouple junctions in the thermopiles between the positive and negative thermocouple elements, and to attach the thermocouple elements to the ceramic components.

28 Claims, 8 Drawing Sheets

(56) References Cited

U.S. PATENT DOCUMENTS

| | | | |
|---|---|---|---|
| 5,288,147 | A | 2/1994 | Schaefer et al. |
| 7,258,482 | B2 * | 8/2007 | Hutter ............... G01K 7/02 374/13 |
| 2001/0019049 | A1 | 9/2001 | Jorimann et al. |
| 2002/0012379 | A1 | 1/2002 | Kinoshita |
| 2003/0231693 | A1 | 12/2003 | Hutter |
| 2005/0169344 | A1 | 8/2005 | Hutter et al. |
| 2008/0052032 | A1 | 2/2008 | Danley |
| 2011/0188534 | A1 | 8/2011 | Nishimura et al. |
| 2012/0134386 | A1 | 5/2012 | Bender et al. |
| 2016/0163948 | A1 * | 6/2016 | Wang ............... H01L 35/34 136/205 |

FOREIGN PATENT DOCUMENTS

| | | | | |
|---|---|---|---|---|
| EP | 1215484 | A | | 6/2002 |
| JP | 56168525 | A * | 12/1981 | ............ H01L 35/34 |
| JP | 05322813 | A | | 12/1993 |
| JP | 2001249093 | A | | 9/2001 |
| JP | 2002181751 | A | | 6/2002 |
| JP | 2004020570 | A | | 1/2004 |
| JP | 2005134397 | A | | 5/2005 |
| JP | 3163711 | U | | 10/2010 |
| WO | 2014153438 | | | 9/2014 |

OTHER PUBLICATIONS

Office Action dated Jan. 25, 2017 in Chinese Application No. 201480029406.0, and English translation thereof.

Office Action dated Nov. 1, 2016 in Japanese Patent Application No. 2016-504356, and translation thereof.

International Preliminary Report on Patentability and Written Opinion of the International Searching Authority dated Oct. 1, 2015 in International Patent Application No. PCT/US2014/031288.

International Search Report and Written Opinion dated Aug. 11, 2014 in PCT/US2014/031288.

Second Office Action in Chinese Patent Application No. 201480029406.0, dated on Oct. 9, 2017; 30 pages.

* cited by examiner

THERMOPILE DIFFERENTIAL SCANNING CALORIMETER SENSOR

This application is the U.S. National Stage of International Application No. PCT/US2014/031288, filed Mar. 20, 2014, entitled "Thermopile Differential Scanning calorimeter Sensor," which claims priority to U.S. Provisional Application No. 61/804,384, filed Mar. 22, 2013, both of which are incorporated by reference herein in their entireties.

BACKGROUND

The present embodiments relate generally to sensors for heat flux differential scanning calorimeters.

Heat flux differential scanning calorimeters (DSCs) generally use a method of measurement based upon a local temperature difference. Heat flux DSCs are twin instruments that measure the difference in heat flow rates between a sample measuring system and a reference measuring system. Most typically, heat flux DSCs measure a single temperature difference between the sample and reference systems.

The measured heat flow rate is taken to be:

$$q = \frac{\Delta T}{R(T)},$$

where $\Delta T$ is the temperature difference measured between the sample and reference systems and $R(T)$ is a temperature dependent proportionality factor that has the dimensions of thermal resistance, i.e., temperature divided by power. For example, the unit may be of measurement $°$ C./watt.

The temperature difference may be measured by any convenient technique, for example by using thermocouples. The temperature difference may be measured by a single differential thermocouple where one thermocouple junction is attached to the sample system and a second thermocouple junction is attached to the reference system, and the two junctions are connected as a differential pair. In a differential pair, the positive leads of the two thermocouples are electrically connected and the temperature difference is measured between the negative leads of the thermocouple pair. Alternatively, the negative leads of the two thermocouples can be electrically connected and the temperature difference is measured between the positive leads of the thermocouple pair.

A useful figure of merit for a DSC sensor is the product of the electrical output of the sensor and the thermal resistance of the sensor. It is a measure of the sensitivity of the sensor, the ratio of electrical output per unit of power, e.g. μvolts/watt. For a differential thermocouple, it is the product of the Seebeck coefficient of the thermocouple and the sensor thermal resistance.

One method for increasing the sensitivity of the sensor is to use a thermopile, which is a number of thermocouples in series, to measure the temperature difference. In a thermopile, an equal number of thermocouple junctions are installed on each of the sample and reference systems. The junctions are connected in series with alternate junctions on the sample and reference systems. For example, the positive lead of a sample junction connects to the positive lead of a reference junction and the negative lead of the sample junction connects to the negative lead of another reference junction.

The junctions are connected in series in this manner until all junctions are connected and there is one free lead wire connected to a reference junction and one free lead wire connected to a sample junction. The free sample and reference lead wires will both be either positive or negative. The differential temperature between the sample and reference systems can be determined from the voltage across these wires. In the case of a thermopile sensor, the sensitivity of the sensor is equal to the product of the number of thermocouple junctions on the sample or reference side, the Seebeck coefficient of the thermocouple pair and the thermal resistance of the sensor. Thus, higher output sensors can be made by using a thermopile to measure the temperature difference.

The prior art includes a number of different methods for constructing thermopile DSC sensors. These include: deposition of the thermopile on an electrically insulating substrate using thin-film techniques, application of the thermopile to an electrically insulating substrate using thick-film techniques such as silk-screen printing, brazing metal thermocouple alloys to one another and to ceramic components, and joining protected electrically insulated thermocouples to a sensor structure comprising a thermal resistance. U.S. Pat. No. 5,033,866 to Kehl et al. and U.S. Pat. No. 5,288,147 to Schaefer et al. disclose thermopile DSC sensors fabricated using thick-film techniques. U.S. Patent Application 2008/0080591 to Tanaka et al. discloses thermopile DSC sensors fabricated by brazing metal thermocouple alloys to one another and to ceramic components. U.S. Patent Application 2011/0188534 to Nishimura et al. discloses thermopile DSC sensors where protected electrically insulated thermocouples are joined to a sensor structure comprising a thermal resistance.

However, each of these construction methods has certain disadvantages. For example, in thermopile sensors constructed by thin-film methods, the thermocouple materials are in the form of thin films that are deposited by evaporation of the materials. This generally limits the selection of material to pure metals, excluding the use of alloys. This restricts the choice of thermocouple materials to thermocouples that have generally low Seebeck coefficients. Therefore, sensors constructed using thin-film techniques tend to have low sensitivity. Given that the deposited films are very thin, the electrical impedance of the thermopile is quite high. This high impedance results in high electrical noise in the electronic circuitry that amplifies the differential temperature signal.

Thick film thermopile DSC sensors also have disadvantages. The thick film materials are a mixture of powdered thermocouple alloys, ceramics, glass frit, binders and organic solvents. They are applied to the substrate in liquid form, often by screen printing, dried and fired to form a solid coating on the substrate. By comparison with solid metal thermocouple alloys, their thermoelectric characteristics may vary considerably because the resultant mixture of powdered metals and binders may be inhomogeneous and may not conform to standards for the given thermocouple type. They also have much higher electrical resistivity than solid alloys and, like thin-film devices, also suffer from high impedance and the attendant amplification noise.

DSC sensors constructed by brazing thermocouple alloys and ceramic components avoid many of these problems but instead have unique problems resulting from the use of brazing. A wide selection of thermocouple alloys may be used and low sensor impedance can be achieved because solid metal thermocouple alloys are used. Brazing is a liquid phase joining process where the braze alloy melts at a lower temperature than the materials being joined, wets the surfaces of the base materials to form intimate contact and solidifies, joining them. Often, the liquid braze alloy dissolves the base materials forming other alloys. The presence of the braze alloy and any intermediate alloys that may form introduces additional thermoelectric materials into the thermopile potentially causing its output to differ from the standard for the thermocouple type. Thus, the output of the thermopile will not match the thermocouple standard, possibly introducing measurement errors.

Also, an important characteristic of a braze alloy for joining a particular alloy or combination of alloys is its ability to wet the base material. Good wetting is essential to forming reliable braze joints. Braze alloys that wet base materials well tend to flow along the surface of the base materials when they melt, making containment of the braze alloy difficult. Braze alloys that coat the surface of the thermocouple alloy may introduce additional thermoelectric elements into the thermopile, altering its output from the standard for the thermocouple type, possibly introducing measurement errors. The ceramic parts of the sensor that are brazed to the thermocouple junctions electrically insulate the thermocouple junctions from one another. If the braze alloy joining a thermocouple junction to a ceramic component flows across the surface of the ceramic, it may form a connection with an adjacent junction shorting the junctions, making the sensor inoperative.

Protected, electrically insulated thermocouples have one or more thermocouples that are surrounded by a ceramic electrical insulator and enclosed within a metal protection tube. When used in a thermopile DSC sensor, the protected thermocouples must be thermally connected to the sensor thermal resistance. In some DSCs, such as the DSC disclosed in U.S. Patent Application No. 2011/0188534, the thermocouple protection tubes may be brazed to the sensor thermal resistance. The ceramic electrical insulation between the thermocouple and the protection tube acts as a thermal insulator between the thermal resistance and the thermocouple. It reduces the sensitivity and speed of response of the thermocouple to sample heat flows that create the temperature differences across the thermal resistances. The thermocouple assemblies may have significant heat capacity which increases the heat capacity of the DSC sensor assembly, reducing its responsiveness and its ability to respond to rapid changes in sample heat flow. To keep the thermocouple heat capacity as low as possible, very small diameter protection tubes are employed, which in turn requires that the thermocouple wires be very fine. For that reason, the thermocouple has a relatively high electrical impedance. This tends to create high noise in the amplifier stages, because the sensor consequently has a high impedance.

Most heat flux DSCs employ a single differential temperature measurement and the simplified measurement method described above. It is well known that the simplified measurement method does not correctly measure the sample heat flow rate under many important experimental conditions. In particular, when a physical transformation occurs in the sample, the sample and reference heating rates are not the same. Consequently the measured heat flow rate may be significantly different from the actual sample heat flow rate. The simplified measurement method is based on the assumption that the DSC is perfectly symmetrical, i.e., the sample measuring system and the reference system are identical. As is well known, perfect symmetry is rarely achieved, such that the resulting heat flow rate measurement generally includes artifacts resulting from the asymmetry between the sample and reference measurement systems. An example is the DSC zero line when the instrument is operated without a sample or a reference. The heat flow rate should be very close to zero, but rarely is. The deviation from zero heat flow rate for an empty instrument is evidence that the instrument is not symmetric as assumed.

SUMMARY

In one aspect, an embodiment is a sensor for a differential scanning calorimeter or DSC. The DSC has a ceramic substrate with a sample side hole and a reference side hole, a sample side thermopile with thermocouple elements of a first polarity and thermocouple elements of a second polarity, and a reference side thermopile with thermocouple elements of the first polarity and thermocouple elements of the second polarity. Segments of the thermocouple elements of the first polarity in the sample thermopiles are diffusion-bonded to segments of the thermocouple elements of the second polarity to form diffusion-bonded sample thermocouple junctions. Segments of the thermocouple elements of the first polarity in the reference thermopile are diffusion-bonded to segments of thermocouple elements of the second polarity to form diffusion-bonded reference thermocouple junctions. The sample side thermopile is positioned over the sample side hole and the sample platform is positioned and centered over the sample side thermopile. The reference side thermopile is positioned over the reference side hole, and the reference platform is positioned and centered over the reference side thermopile. Outer arc segments of thermocouple elements of the first polarity are diffusion bonded to the ceramic substrate. The sample thermopile has inner arc segments of thermocouple elements of the second polarity that are diffusion bonded to the sample platform, and the reference thermopile has inner arc segments of thermocouple elements of the second polarity that are diffusion bonded to the reference platform.

In another aspect, an embodiment is a differential scanning calorimeter that has a measurement chamber with a thermopile sensor. The thermopile sensor includes a sample side thermopile and a reference side thermopile on a ceramic substrate. The sample side thermopile has thermocouple elements of a first polarity and thermocouple elements of a second polarity. Segments of the thermocouple elements of the first polarity in the sample side thermopile are diffusion-bonded to segments of the thermocouple elements of the second polarity to form thermocouple junctions. The reference side thermopile also has thermocouple elements of the first polarity and thermocouple elements of the second polarity. The segments of the thermocouple elements of the first polarity in the reference thermopile are diffusion-bonded to segments of the thermocouple elements of the second polarity to form thermocouple junctions. A sample platform is positioned and centered over the sample side thermopile, and a reference platform is positioned and centered over the reference side thermopile. Outer arc segments of thermocouple elements of the first polarity from both thermopiles are diffusion bonded to a ceramic substrate. The sample thermopile has inner arc segments of thermocouple elements of the second polarity that are diffusion bonded to the sample platform, and the reference thermopile has inner arc segments of thermocouple elements of the second polarity that are diffusion bonded to the reference platform.

In another aspect, an embodiment is a sensor that has a ceramic substrate with a raised flat surface surrounding a hole. A thermopile is positioned over the hole and supported on the raised flat surface. The thermopile has positive thermocouple elements and negative thermocouple elements. Segments of the positive thermocouple elements are diffusion bonded to segments of the negative thermocouple elements to form diffusion bonded thermocouple junctions. A platform is centered over the thermopile. Outer arc segments of the positive and negative thermocouple elements are diffusion bonded to the ceramic substrate. Inner arc segments of the positive and negative thermocouple elements are diffusion bonded to the platform.

In another aspect, an embodiment is a twin thermopile sensor for a heat flux differential scanning calorimeter. It has a ceramic substrate with a sample side thermopile centered on a sample position and a reference side thermopile centered on the reference position. The sample side thermopile has thermocouple elements of a first polarity and thermocouple elements of a second polarity that are diffusion bonded to each other to form thermocouple junctions, and the reference side thermopile has thermocouple elements of the first polarity and thermocouple elements of the second polarity that are diffusion bonded to each other to form thermocouple junctions. A sample platform is centered on the sample side thermopile and a reference platform is centered on the reference side thermopile. Outer arc segments of the thermocouple elements from both the sample and reference thermopiles are diffusion bonded to the ceramic substrate. Inner arc segments of the thermocouple elements in the sample thermopile are diffusion bonded to the sample platform, and inner arc segments of thermocouple elements in the reference thermopile are diffusion bonded to the reference platform.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

DETAILED DESCRIPTION

Figure 1:
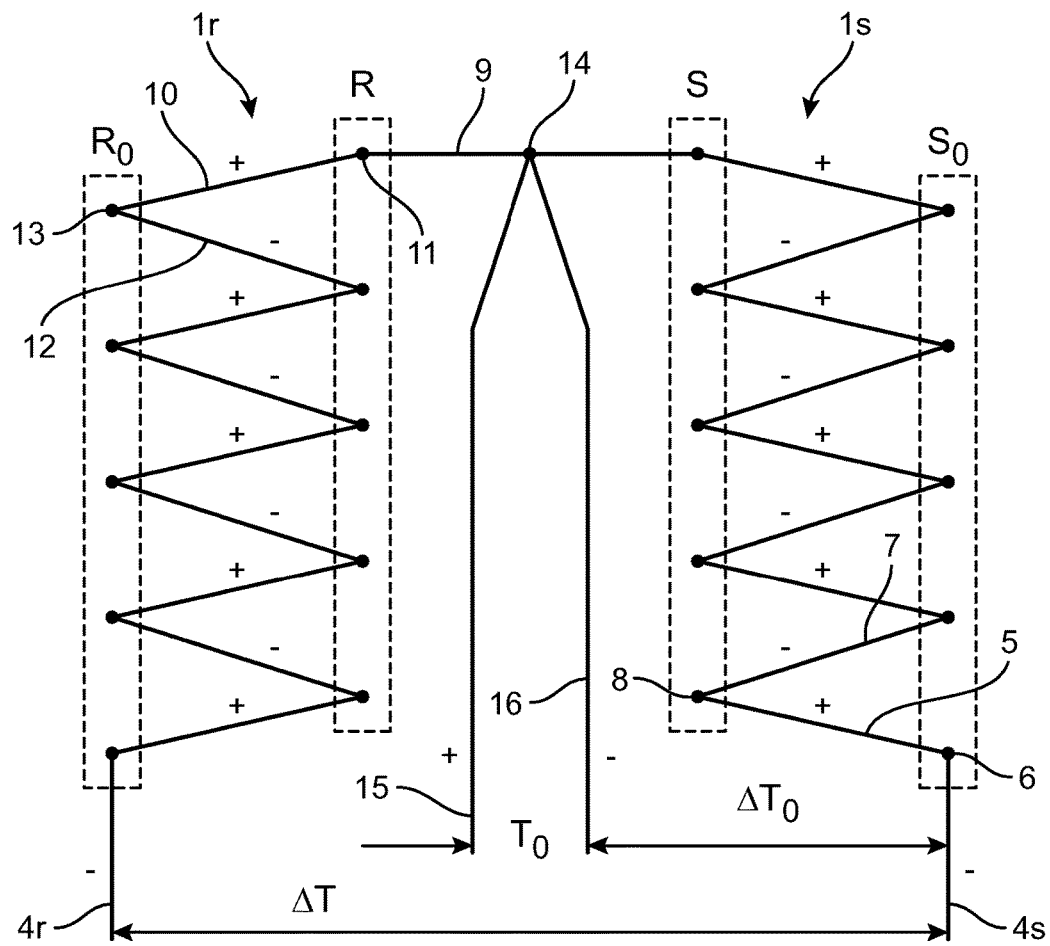
FIG. 1 is an electrical schematic of an exemplary embodiment of a diffusion bonded thermopile DSC sensor.

FIG. 1 is a schematic diagram of an exemplary thermopile DSC sensor that comprises metal alloy thermocouples and ceramic components. In this embodiment, the thermocouple junctions between the thermocouple alloys are made by diffusion bonding, as are the structural and thermally conductive joints between the thermocouple alloys and the ceramic parts. Diffusion bonding is a solid state joining process in which the surfaces to be joined are brought into intimate contact under pressure and are heated in a protective atmosphere appropriate for the materials being joined. The heat and pressure are maintained for a sufficient period of time such that the materials interdiffuse, joining them together.

The high output thermocouple pairs of this embodiment offer numerous advantages. The source impedance of the resulting sensor may be kept low, formation of intermediate alloys may be avoided, unwanted braze alloy flow may also be avoided and the output of the resulting thermocouples matches the standards for the thermocouple type. The thermopile DSC sensor in this embodiment is configured to include two differential temperature measurements. This sensor uses the measurement methods disclosed in U.S. Pat. Nos. 6,431,747 and 7,470,057, which are both incorporated by reference herein in their entireties.

FIG. 1 is a schematic of an exemplary twin thermopile DSC sensor showing the connection of the thermocouples and how the signals are measured. The sample thermopile $1s$ measures the temperature difference between a sample measurement region S and a sample base region $S_0$. The sample in a sample container is installed on the sample measurement region of the sensor. The sample measurement and sample base regions each have an equal number of thermocouple junctions joined to them.

The reference thermopile $1r$ measures the temperature difference between a reference measurement region R and a reference base region $R_0$. The reference sample, if used, in a reference container is installed on the reference measurement region of the sensor. In most instances, the reference container does not contain a reference sample. The reference measurement and reference base regions each have an equal number of thermocouple junctions joined to them that is the same as the number of thermocouple junctions in the sample measurement and base regions. Each thermocouple junction is the connection between a positive and a negative thermocouple element. In the sample thermopile, each thermocouple junction is physically joined to either the sample measurement region or to the sample base region. In the reference thermopile, each thermocouple junction is physically joined to the reference measurement region or to the reference base region.

In the sample thermopile, a negative wire $4s$ joins a positive thermocouple element 5 in the sample base region $S_0$ to form the first thermocouple junction 6. Positive thermocouple element 5 joins negative thermocouple element 7 in the sample measurement region S to form thermocouple junction 8. Negative thermocouple element 7 then joins another positive thermocouple element to form a second thermocouple junction in the sample base region $S_0$. This pattern continues such that a series of thermocouple junctions are formed alternately in the sample base and sample measurement regions. Thus N thermocouple junctions are created in the sample base region.

The last thermocouple junction number N in the sample measurement region is created by the junction of the positive element connected to junction N in the sample measurement region and a negative element 9 that connects to a positive element 10 forming the first junction 11 in the reference measurement region R.

In the reference thermopile, the positive thermocouple element 10 connects to a negative thermocouple element 12 in the reference base region $R_0$ to form the first reference base region junction 13. Negative thermocouple element 12 then joins another positive thermocouple element to form a second thermocouple junction in the reference measurement region R. This pattern continues with a series of thermocouple junctions formed alternately in the reference measurement and reference base regions. Thus N thermocouple junctions are created in the reference measurement region.

The last thermocouple junction number N in the reference base region is created by the junction of the positive element connected to junction N in the reference measurement region and a negative wire 4r. Thus, two connected thermopiles of N pairs each of thermocouple junctions are created between the sample measurement and sample base regions and between the reference measurement and reference base regions.

A thermocouple 14 comprising positive thermocouple element 15 and negative thermocouple element 16 is joined to the negative thermocouple element 9, thus joining the two thermopiles between the sample measurement and reference measurement regions. Differential temperature measurement $\Delta T$ is measured between negative thermocouple wires 4s and 4r that terminate each thermopile in base regions $S_0$ and $R_0$. Differential temperature measurement $\Delta T_0$ is measured between negative thermocouple wire 4s terminating sample thermopile 1s and negative thermocouple wire 16 of thermocouple 14.

The positive and negative thermocouple elements may be interchanged with no change in the performance of the sensor. It only requires that the correct sign be included in the equations that convert thermopile and thermocouple voltages to differential temperature and temperature measurements. Although FIG. 1 illustrates five junction pairs in each thermopile, the number of junction pairs N may be any number greater than 1. The choice depends on the objectives of the designer and the number of junctions that can fit within a sensor given its physical size.

As illustrated in FIG. 1, the thermopile output is positive. If the temperature of the sample measurement region is higher than the temperature of the sample base region, the voltage measured between wires 16 and 4s will be positive with respect to 4s. If the temperature of the sample measurement region is higher than the temperature of the reference measurement region, the voltage measured between wires 4s and 4r will be positive with respect to 4r.

The heat flow measurement method of the '747 and '057 patents is based on measuring sample and reference calorimeter heat flow rates independently using the following equations:

$$q_s = \frac{\Delta T_0}{R_s} - C_s \dot{T}_s$$

$$q_r = \frac{\Delta T_0 + \Delta T}{R_r} - C_r(\dot{T}_s - \Delta \dot{T})$$

The dot above $T_s$ and $\Delta T$ indicates differentiation with respect to time, i.e., it indicates a heating rate. When a thermopile sensor is used with these heat flow rate equations, the differential temperature measurement conversions from voltage to temperature must account for the number of junctions in the thermopile:

$$\Delta T = \frac{V(\Delta T)}{NS(\Delta T)}$$

$$\Delta T_0 = \frac{V(\Delta T_0)}{NS(\Delta T_0)}$$

where $V(\Delta T)$ is the voltage developed across the thermopiles by the difference between the sample and reference measurement region temperatures and $V(\Delta T_0)$ is the voltage developed in the sample thermopile between the sample measurement and sample base region temperatures. S(T) is the Seebeck coefficient for the thermocouple type used in the thermopile at the sample or reference measurement region temperature. Sample and reference temperatures are obtained using measured temperature $T_0$ and the differential temperature measurements in accordance with the '747 and '057 patents using the following equations:

$$T_s = T_0 - \Delta T_0, T_r = T_s - \Delta T$$

All calculations are performed as specified in the '747 and '057 patents.

Figure 2:
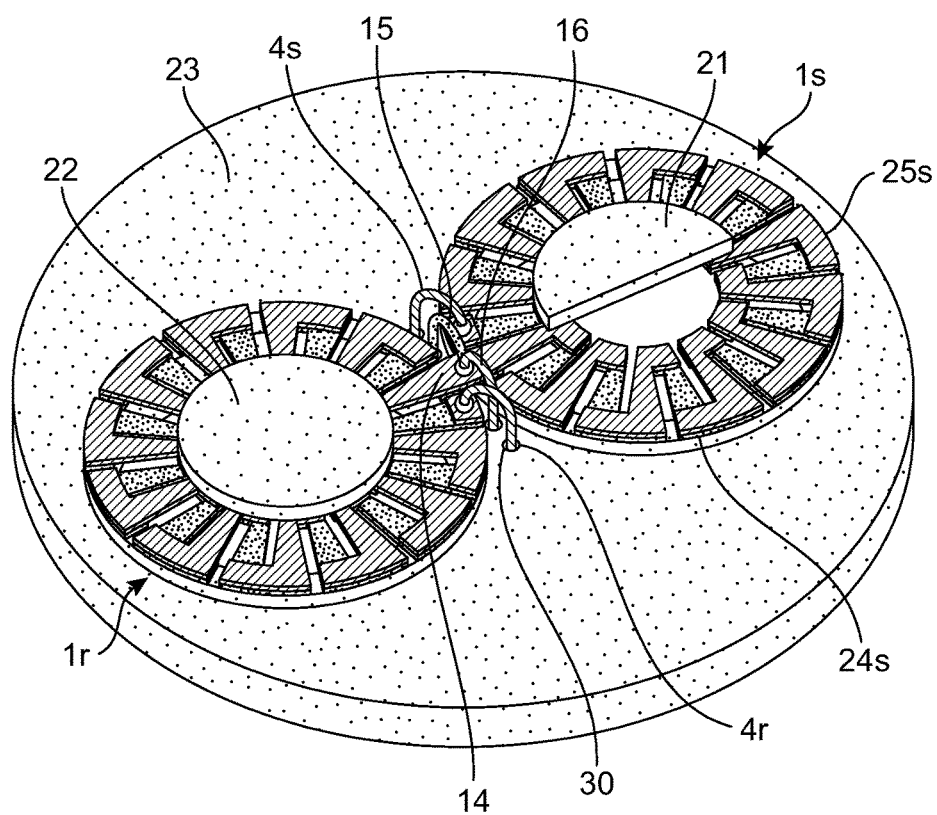
FIG. 2 is a perspective view of an embodiment of a diffusion bonded thermopile DSC sensor.

FIG. 2 shows a perspective view of a diffusion bonded thermopile DSC sensor having the configuration of FIG. 1 with twelve thermocouple pairs in each thermopile. The sensor assembly comprises a ceramic sample platform 21 in the form of a circular disk, a ceramic reference platform 22 in the form of a circular disk, a ceramic substrate 23, a sample thermopile 1s comprising metal alloy thermocouple elements of a first polarity (e.g., positive) and metal alloy thermocouple elements of a second opposite polarity (i.e., negative if the first polarity is positive), a reference thermopile 1r comprising positive metal alloy thermocouple elements and negative metal alloy thermocouple elements, thermocouple lead wires 4s and 4r and a thermocouple 14. Thermocouple lead wires 4s, 4r, 15 and 16 are fed down through holes 30 in ceramic substrate 23 and are connected to the heat flow measurement system.

In FIG. 2, half of the sample platform is cut away to show thermocouple junctions in the sample measurement region. For example, sample thermopile 1s can be made of a thin sheet of positive thermocouple alloy 24s which is diffusion bonded to the ceramic base structure 23 and a thin sheet of negative thermocouple alloy of 25s which is diffusion bonded to the side of the positive thermocouple alloy sheet opposite the side of the positive thermocouple alloy that is bonded to the ceramic base structure. The sample platform 21 and the reference platform 22 are diffusion bonded to the central portions of the surface of their respective negative thermocouples.

A structure equivalent to the structure described in the preceding paragraph may be fabricated by substituting negative thermocouple alloys for the positive thermocouple alloys and substituting positive thermocouple alloys for the negative thermocouple alloys.

Figure 3:
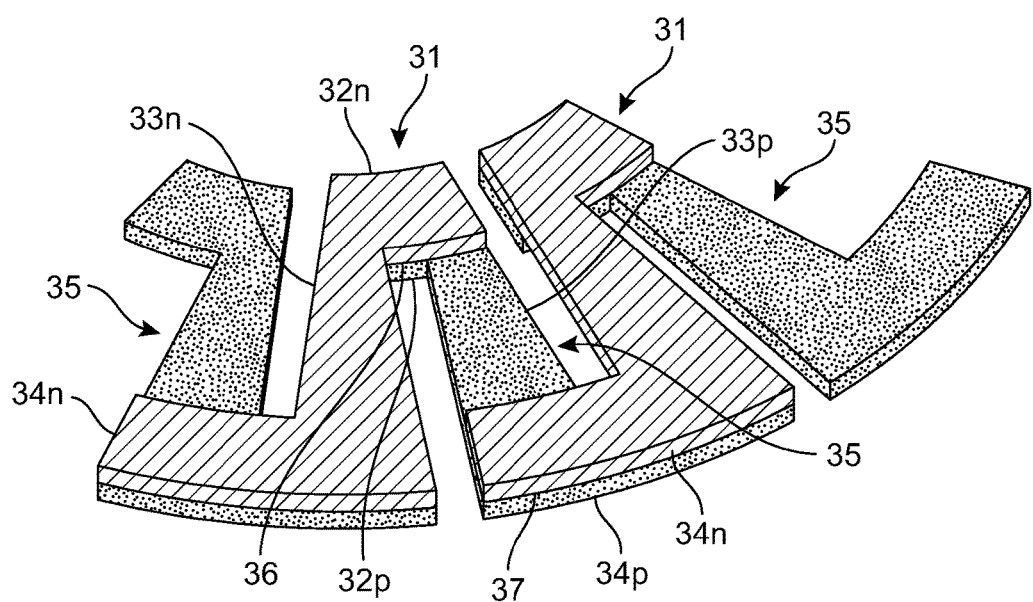
FIG. 3 is a perspective view of a portion of a thermopile showing positive and negative thermocouple elements.

FIG. 3 illustrates a portion of one of the thermopiles including three positive thermocouple elements 35 and two negative thermocouple elements 31. Each of the negative thermocouple elements 31 has an inner section 32n that is an arc segment extending outward from one end of a tapered section 33n. An outer section 34n is an arc segment that extends outward from the opposite end of the tapered section. The inner and outer arc segments are concentric and arranged so that they extend outward from opposite edges of the tapered section and both arc segments subtend the same angle. Each of the positive thermocouple elements 35 has an inner section 32p that is an arc segment extending outward from one end of a tapered section 33p. An outer section 34p is an arc segment that extends outward from the opposite end of the tapered section.

The inner and outer arc segments are concentric and arranged so that they extend outward from opposite edges of the tapered section and both arc segments subtend the same angle. Thus, each of the positive and negative thermocouple elements has a "Z shape" where the top and bottom of the Z are concentric arc segments subtending the same angle and the part of the Z connecting the top and bottom arc segments is a tapered segment.

A positive thermocouple element and a negative thermocouple element are arranged so that the inner arc segment 32n of the negative thermocouple element overlaps and coincides with the inner arc segment 32p of the positive thermocouple element forming a measuring region thermocouple junction 36 where the coincident positive and negative thermocouple elements overlap and are diffusion bonded together. The positive and negative thermocouple elements are arranged in opposite orientation so that the tapered section 33n of the negative thermocouple element is adjacent to one end of the coincident overlapping inner arc segments and the tapered section 33p of the positive thermocouple element is adjacent to the other end of the overlapping inner arc segments.

The positive and negative tapered segments are offset angularly from one another and do not touch. Thus, the positive and negative thermocouple elements 31 and 35 comprise a measuring region thermocouple where the thermocouple junction 36 is formed where the inner arc segments 32n and 32p coincide and are diffusion bonded together. The outer arc segments 34n and 34p are offset from each other, extending outward from their respective tapered segments in opposite directions and do not overlap.

An adjacent thermocouple pair comprising negative thermocouple element 31 and positive thermocouple element 35 is arranged such that the outer arc segment of the negative element 34n of the adjacent thermocouple pair overlaps and coincides with and is diffusion bonded to the outer arc segment 34p of the positive element of the first thermocouple pair. This forms a base region thermocouple junction between the two adjacent thermocouples. Additional thermocouple pairs are added in this fashion, forming a flat circular thermopile in which the thermocouple junctions at the inside diameter are in either the sample measuring region or the reference measuring region, and the thermocouple junctions at the outside diameter are in the sample base region or the reference base region, respectively.

Figure 4:
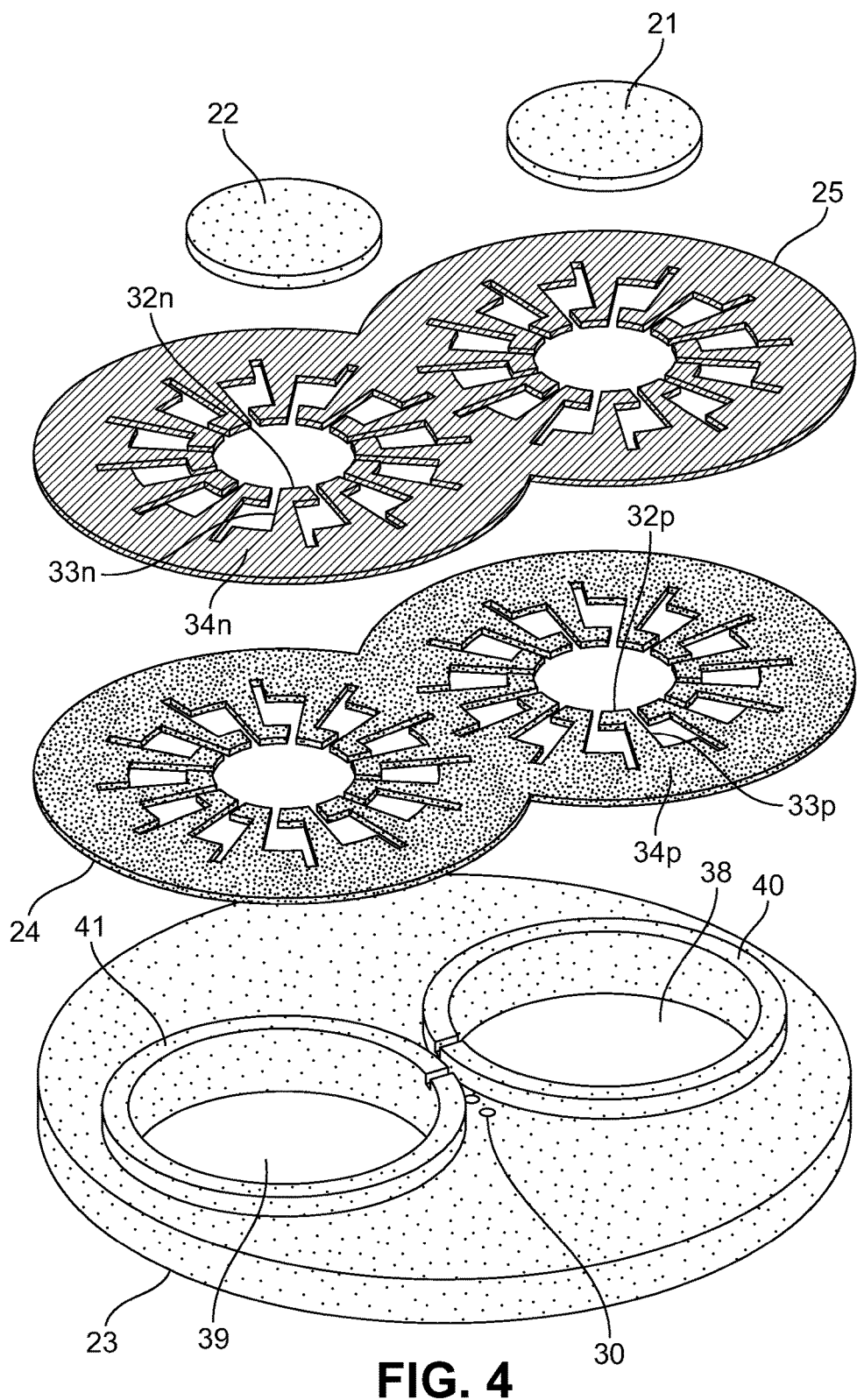
FIG. 4 is an exploded view of showing the different layers of a thermopile DSC sensor during fabrication.

FIG. 4 is an exploded view of the diffusion bonded sensor showing how sample platform 21 and reference platform 22, ceramic base 23, positive thermocouple element sheet 24 and negative thermocouple element sheet 25 are diffusion bonded together to form the thermopiles. As shown in FIGS. 2 and 3 the positive thermocouple elements 31 and negative thermocouple elements 35 are individual "Z-shaped" pieces of thin sheet thermocouple alloy that are diffusion bonded to overlapping thermocouple elements of opposite polarity and to the ceramic base and ceramic sample and reference platforms. To avoid the difficulty of aligning and maintaining alignment of a multitude of small individual thermocouple elements, the positive thermocouple elements and the negative thermocouple elements are formed in a sheet where they are all joined together for diffusion bonding. After diffusion bonding, the thermocouple sheets are trimmed to separate the individual thermocouples.

Positive thermocouple alloy sheet 24 is bounded by two intersecting circles of equal diameter. The center distance of the two circles is equal to the center distance between the sample and reference platforms and between the two thermopiles. Two patterns, concentric with the two bounding circles, are cut through the sheet. Each of the cutout patterns forms the inner arc segments 32p, the tapered sections 33p and the inner circular edge and the two straight edges of the outer arc segments 34p. The outer circular edges of the outer arc segments 34p are not cut through. Thus, the twelve positive thermocouple elements 35 formed by each cutout are joined to the sheet along their outer circular edge. In this manner, all of the twenty-four positive thermocouple elements of the sample and reference thermopiles are part of positive thermocouple alloy sheet 24.

In a similar manner, negative thermocouple alloy sheet 25 is bounded by two intersecting circles of equal diameter. The center distance of the two circles is equal to the center distance between the sample and reference platforms and between the two thermopiles. Two patterns, concentric with the two bounding circles, are cut through the sheet. Each of the cutouts form the inner arc segments 32n, the tapered sections 33n and the inner circular edge and the two straight edges of the outer arc segments 34n. The outer circular edges of the outer arc segments 34p are not cut through. Thus the twelve negative thermocouple elements 31 formed by each cutout are joined to the sheet along their outer circular edge. In this manner, all of the twenty-four negative thermocouple elements of the sample and reference thermopiles are part of negative thermocouple alloy sheet 25.

Ceramic base 23 has a circular sample side hole 38 through ceramic base 23 that is concentric with the sample platform and sample thermopile. Ceramic base 23 also has a circular reference side hole 39 through ceramic base 23 that is concentric with the reference platform and reference thermopile. The diameter of the holes is equal to the diameter of the inner edge of the positive thermocouple element outer arc segment 34p. and to the diameter of the inner edge of the negative thermocouple element outer arc segment 34n, as shown in the figures. The diameter of the sample side hole and the reference side hole defines the inner diameter of the sample base region and the inner diameter of the reference base region of the two thermopiles, respectively.

Raised flat surface 40 surrounds sample side hole 38. Its outside diameter is the same as the diameter of the outer edge of positive and negative outer arc segments 34p and 34n. Raised flat surface 41 surrounds reference side hole 39. Its outside diameter is the same as the diameter of the outer edge of positive and negative outer arc segments 34p and 34n. Raised flat surfaces 40 and 41 are coplanar.

To diffusion bond the assembly, positive thermocouple alloy sheet 24 is positioned on raised platforms 40 and 41 with the inner edges of outer arc segments 34p aligned with the circumference of sample side hole 38 and with the circumference of reference side hole 39. Negative thermocouple alloy sheet 25 is laid on top of positive thermocouple alloy sheet 24 in the orientation shown with the inner edges of outer arc segments 34n aligned with the diameter of sample side hole 38 and reference side hole 39 and the inner edges of positive outer arc segments 34p. This positions inner arc segments 32p and 32n such that they overlap to form the sample and reference measurement region thermocouples, respectively. It also positions outer arc segments 34p and 34n such that they overlap and form the sample and reference base region thermocouples.

Sample ceramic platform 21 and reference ceramic platform 22 are located on the top surface of negative thermocouple alloy sheet 25. The edge of each platform has the same diameter as the outer edge of inner arc segments 32p and 32n. The edges of the platforms are located concentrically with the outer edges of inner arc segments 32p and 32n.

The entire assembly is installed in a diffusion bonding apparatus. An exemplary apparatus is described below with reference to FIG. 8. Pressure is applied to the bonding surfaces. The apparatus is then heated to the bonding temperature under the requisite protective atmosphere and maintained at the bonding temperature for a sufficient time that diffusion bonds are formed (a) between the raised flat surfaces of the ceramic substrate and the outer arc segments of the positive thermocouple alloy sheet; (b) between the positive and negative thermocouple alloy sheets where the outer arc segments coincide forming the base region thermocouples and where the inner arc segments coincide forming the measurement region thermocouples; and (c) between the inner arc segments of the negative thermocouple sheet and the sample and reference ceramic platforms. For example, Platinel® or other types of thermocouples may be diffusion bonded to the ceramic structures at temperatures ranging from 1100° C. to 1400° C., under an applied pressure of 3-5 MPa for 0.5 to 10 hours, in air, nitrogen or in an inert atmosphere such as helium.

Figure 5:
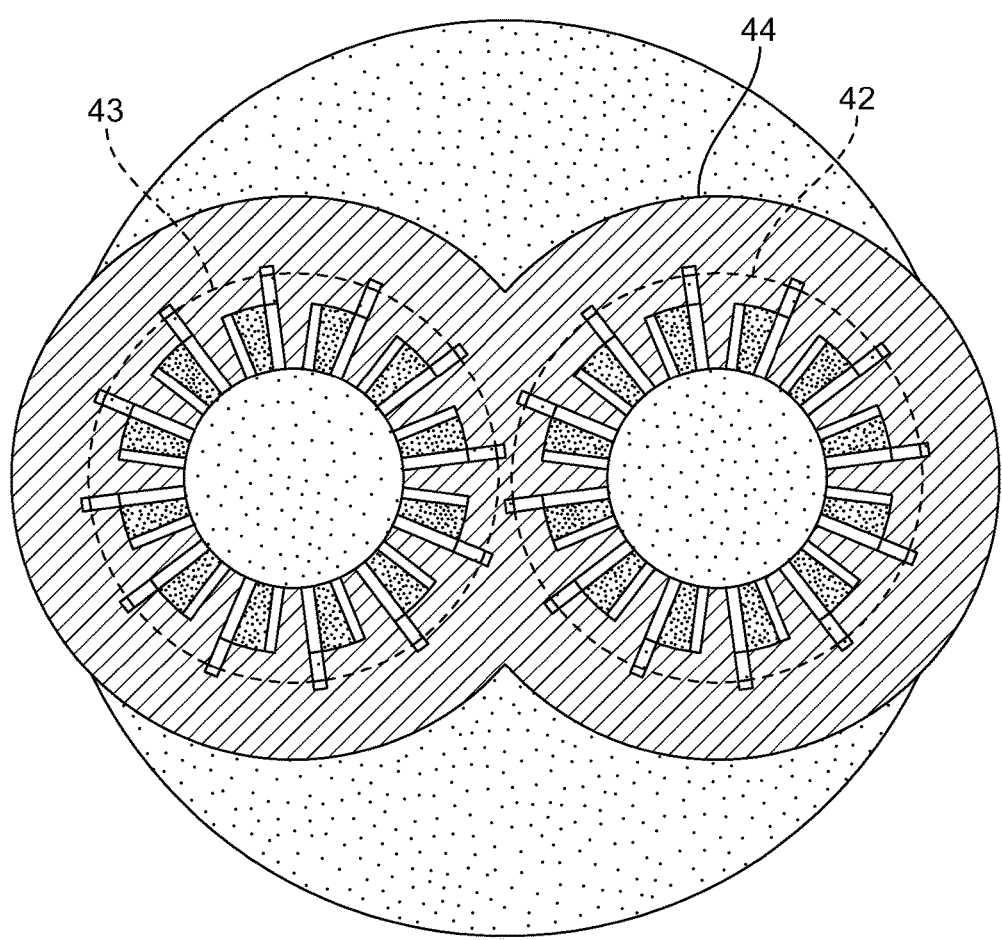
FIG. 5 is a top view of a thermopile sensor after diffusion bonding.

FIG. 5 shows the DSC sensor assembly after diffusion bonding. All of the thermocouple junctions have been formed by diffusion bonding between the positive and negative thermocouple alloys. The thermopiles have been diffusion bonded to the ceramic base structure in the sample and reference base regions and the sample and reference platforms have been diffusion bonded to the thermopiles in the sample and reference measurement regions. The thermocouple alloy sheets have to be trimmed and cut to create a usable sensor because otherwise the junctions in the base regions would be shorted by the excess material beyond the outer edges of the outer arc segments.

The two sheets are trimmed in one operation. The material between the outer edge 42 of the sample thermopile and the outer edge 43 of the reference thermopile, respectively, and the perimeter 44 of the positive and negative sheets is removed. However, a bridge of positive and negative thermocouple alloy between the two thermopiles is left in place to link the sample and reference measuring region thermopiles, as discussed with reference to FIG. 6 below.

Figure 6:
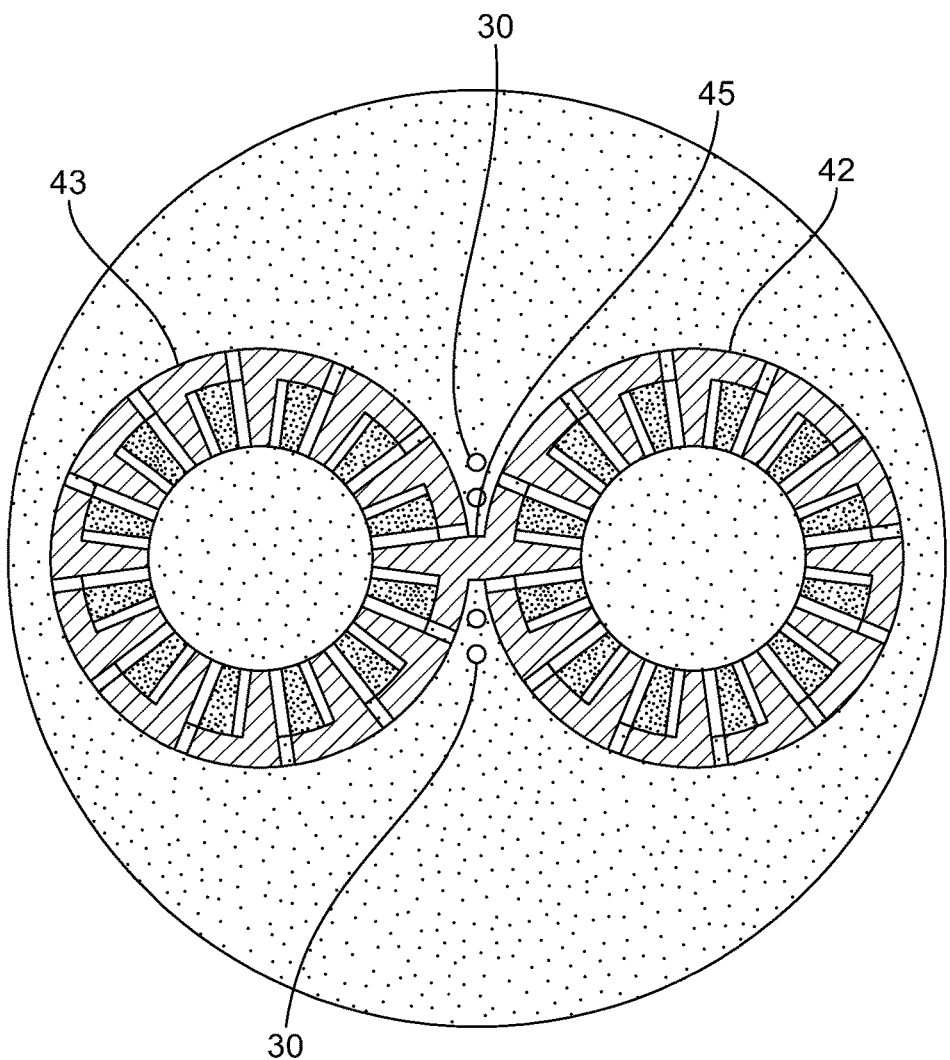
FIG. 6 is a top view of the thermopile sensor of FIG. 5, after the thermocouple alloy sheets have been trimmed.

FIG. 6 shows the sensor after the thermocouple alloy sheets have been trimmed leaving bridge 45 between the sample and reference thermopiles. A cut must also be made through each thermopile in the base region adjacent to the bridge to create the termination of each thermopile to which the negative thermocouple wires are attached. FIG. 6 also shows holes the four holes 30 in the ceramic substrate through which the lead thermocouple wires pass to connect the thermopiles to the temperature measuring system.

Figure 7:
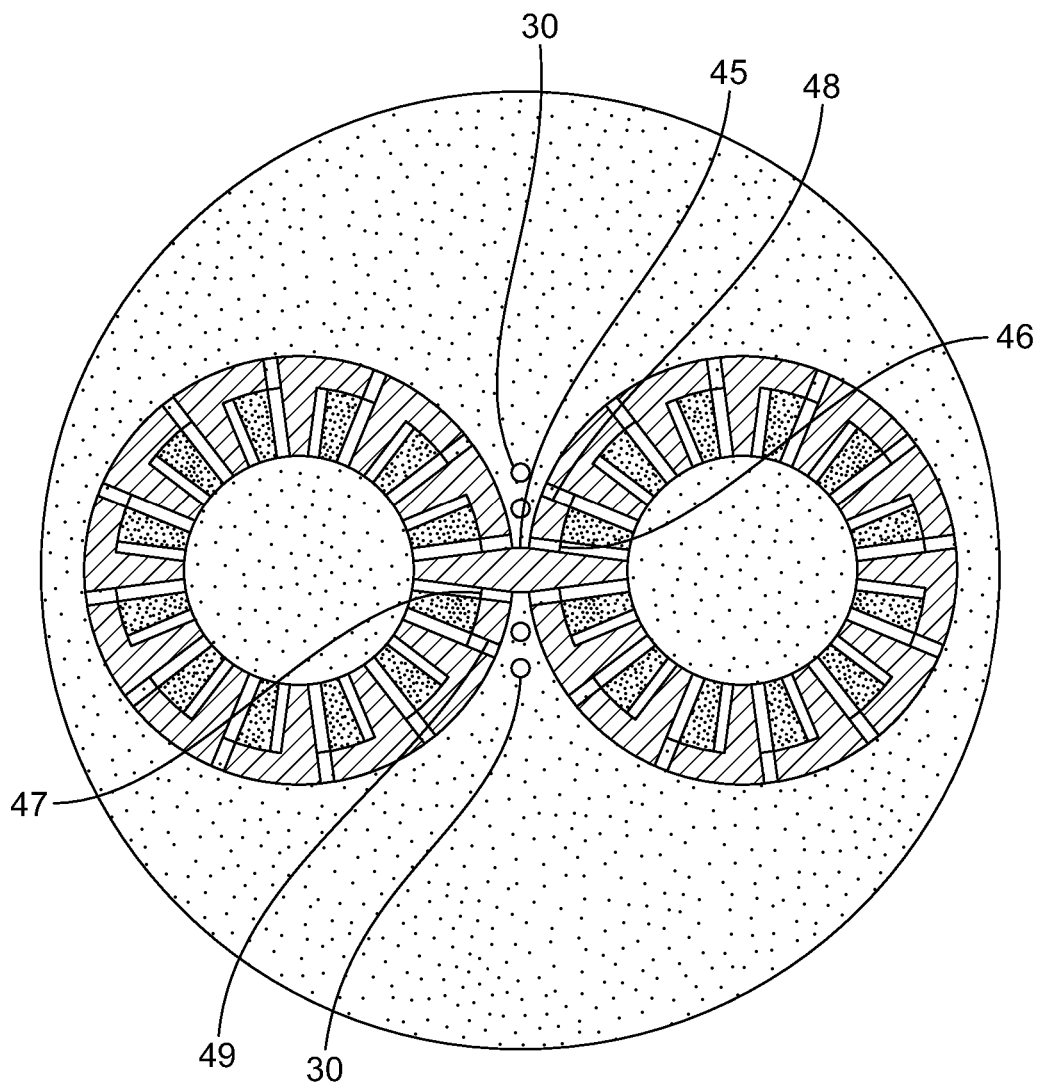
FIG. 7 is a top view of the thermopile sensor of FIGS. 5 and 6, after additional cuts have been made through the negative and position sheets.

FIG. 7 shows the sensor after cut 46 is made through the negative and positive sheets in the sample base region forming termination 48 and cut 47 is made through the negative and positive sheets in the reference base region forming termination 49. As shown in FIG. 2, negative thermocouple wire 4s is attached to the negative termination 48 of the sample base region thermopile, a negative thermocouple wire 4r is attached to the negative termination 49 of the reference base region thermopile and a thermocouple 14 is attached to the bridge 45 between the sample and reference thermopiles.

Figure 8:
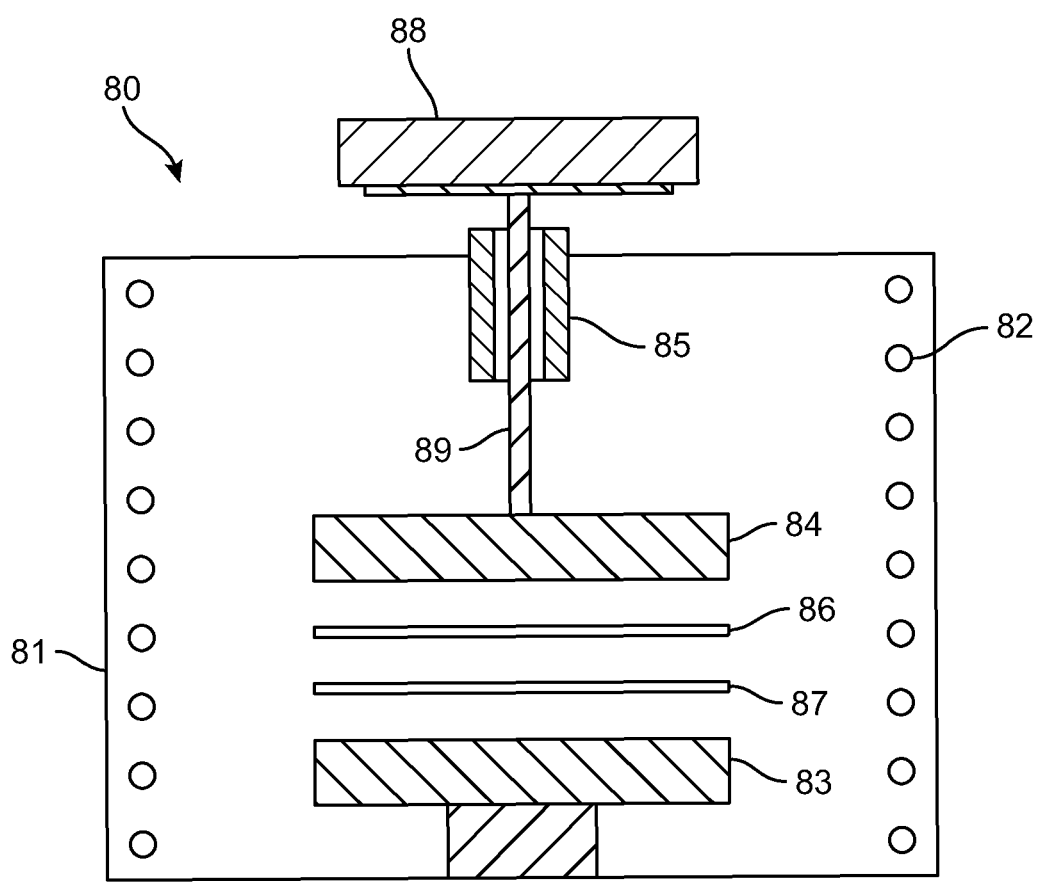
FIG. 8 is schematic diagram of an example of a diffusion bonding apparatus that may be used to fabricate the sensor.

FIG. 8 is schematic diagram of an example of a diffusion bonding apparatus that may be used to fabricate the sensor. Diffusion bonding apparatus 80 has a furnace 81 heated electrically using heating elements 82. Top layer 86 and bottom layer 87 are positioned between bottom anvil 83 and top anvil 84. A support rod 89 is held in position by guide 85 such that it can slide up and down within the guide. Support rod 89 holds a weight 88 that can be used to apply pressure to the two layers 86 and 87 as they are bonded together. While the figure shows two layers being bonded together, it is understood that a multiplicity of layers may be bonded together.

In an exemplary embodiment, the DSC sensor is fabricated using Platinel® thermocouples having positive alloy 55 Pd 31 Pt 14 Au and negative alloy 65 Au 35 Pd wires on a beryllium oxide (BeO) ceramic substrate. Platinel is chosen because it has a high output over a broad range of temperatures, is resistant to oxidation and corrosion, is thermoelectrically stable and operates reliably from −180° C. to 1300° C. BeO is chosen because it has very high thermal conductivity, forms strong diffusion bonds with both positive and negative Platinel alloys, and is available with flat polished surfaces. Other ceramics that have high thermal conductivity, such as AlN and sapphire, may be used, as long as they can bond to the thermocouple alloys being used.

The estimated performance of the thermopile DSC sensor with twelve junction pairs as described above may be compared to that of the DSC sensor described in the '057 patent that is based on a single type E differential thermocouple. The table below compares thermal resistance, heat capacity, time constant and sensitivity for the two sensors at 20° C. In this table, R is the thermal resistance in ° C./watt, C is the heat capacity in joules/° C., and T is the time constant of the sensor in seconds (which is the product of thermal resistance and heat capacity). S is the sensitivity in microvolts/watt which is, as explained above, the product of Seebeck coefficient, thermal resistance and the number of thermocouple junction pairs in the sensor. In general, increasing the thermal resistance increases the sensitivity but increases the time constant, reducing the speed of response. Increasing the heat capacity increases the time constant, reducing the speed of response while not affecting the sensitivity.

|  | R/° C./W | C/J/° C. | T/S | S/μV/W |
| --- | --- | --- | --- | --- |
| Prior art (type E) | 34.5 | .0406 | 1.40 | 2086 |
| Thermopile | 30.8 | .0388 | 1.04 | 11526 |

The thermopile sensor of the exemplary embodiment has a time constant that is 74% of the '057 sensor, indicating a faster response to thermal events occurring in the sample under analysis. In the example shown in the table above, the sensitivity of the thermopile is 5.5 times greater than the '057 sensor, indicating greater sensitivity to weak thermal events occurring in the sample.

Depending upon the desired performance objectives, the geometry and the configuration of the thermopile sensor may be modified to change the thermal resistance, heat capacity, time constant and sensitivity. For example, the thermal resistance is essentially determined by the resistance to heat flow through the thermopiles between the ceramic base structure and the sample or reference platform. It depends mainly on the length and cross-sectional area of the tapered segments 33*p* and 33*n* of the thermocouple elements and on the thermal conductivity of the thermocouple alloys. Increasing the length of the tapered segments increases the thermal resistance, while increasing the cross-sectional area reduces the thermal resistance.

Heat capacity is determined by the specific heat capacity of the materials of construction and their mass which depends on their density and volume. Generally, the heat capacity of the sensor comprises principally the heat capacity of the sample or reference platform plus some fraction of the heat capacity of the positive and negative thermocouple elements. Increasing the thickness of the sample and reference platforms increases the sensor heat capacity and increases the time constant of the sensor. Increasing the cross sectional area of the thermocouple elements tends to increase the sensor time constant as does increasing the length of the tapered sections of the thermocouple elements. The sensitivity of the sensor is proportional to the number of pairs of thermocouple junctions in each thermopile.

The thermopile DSC sensor may be installed within a measurement chamber that heats and cools the sensor, sample container, reference container and sample and provides a uniform temperature environment. DSC enclosures and heating and cooling systems of conventional construction are suitable for use with this invention. For example, U.S. Pat. No. 6,523,998, which is incorporated by reference herein in its entirety, describes a suitable measurement chamber and heating and cooling means. The quasiadiabatic DSC structure and the heat flow rate measurement method disclosed in Provisional Patent Application No. 61/696,488, which is incorporated by reference herein in its entirety, may also be used.

While various embodiments have been described, the description is intended to be exemplary, rather than limiting and it will be apparent to those of ordinary skill in the art that many more embodiments and implementations are possible that are within the scope of the embodiments herein. Accordingly, the embodiments are not to be restricted except in light of the attached claims and their equivalents. Also, various modifications and changes may be made within the scope of the attached claims.

What is claimed is:

1. A sensor for a differential scanning calorimeter comprising:
a ceramic substrate comprising a sample side hole and a reference side hole;
a sample side thermopile comprising a first plurality of thermocouple elements of a first polarity and a second plurality of thermocouple elements of a second polarity, wherein segments of the thermocouple elements of the first polarity are diffusion-bonded to segments of the thermocouple elements of the second polarity to form a plurality of diffusion-bonded sample thermocouple junctions, and wherein said sample side thermopile is positioned over the sample side hole;
a reference side thermopile comprising a third plurality of thermocouple elements of the first polarity and a fourth plurality of thermocouple elements of the second polarity, wherein segments of the thermocouple elements of the first polarity are diffusion-bonded to segments of the thermocouple elements of the second plurality to form a plurality of diffusion-bonded reference thermocouple junctions, and wherein said reference side thermopile is positioned over the reference side hole;
a sample platform positioned and centered over the sample side thermopile; and
a reference platform positioned and centered over the reference side thermopile,
wherein the first plurality of the thermocouple elements comprise outer arc segments that are diffusion bonded to the ceramic substrate and the third plurality of thermocouple elements comprises outer arc segments that are diffusion bonded to the ceramic substrate;
wherein the second plurality of thermocouple elements comprises inner arc segments that are diffusion bonded to the sample platform, and the fourth plurality of thermocouple elements comprises inner arc segments that are diffusion bonded to the reference platform, and
wherein the second polarity is opposite to the first polarity.

2. The sensor of claim 1, wherein the first polarity is positive and the second polarity is negative.

3. The sensor of claim 1, wherein the first plurality of thermocouple elements and the third plurality of thermocouple elements are alloys containing Pd, Pt and Au, and the second plurality of thermocouple elements and the fourth plurality of thermocouple elements are alloys containing Au and Pd.

4. The sensor of claim 1, wherein the first polarity is negative and the second polarity is positive.

5. The sensor of claim 1, wherein the second plurality of thermocouple elements and the fourth plurality of thermocouple elements are alloys containing Pd, Pt and Au and the first plurality of thermocouple elements and the third plurality of thermocouple elements are alloys containing Au and Pd.

6. The sensor of claim 1, comprising a bridge between the sample thermopile and the reference thermopile.

7. The sensor of claim 1, wherein the ceramic substrate comprises a raised flat surface surrounding the sample side hole and a raised flat surface surrounding the reference side hole.

8. The sensor of claim 7, wherein the raised flat surface surrounding the sample side hole and the raised flat surface surrounding the reference side hole are co-planar.

9. The sensor of claim 1, wherein the sample side hole is circular and has a circumference, and inner edges of the outer arc segments of the first plurality of thermocouple elements are aligned with the circumference of the sample side hole.

10. The sensor of claim 1, wherein one of the second plurality of thermocouple elements is connected to one of the third plurality of thermocouple elements.

11. The sensor of claim 1, wherein each thermocouple element of the first plurality of thermocouple elements and the third plurality of thermocouple elements and each thermocouple element of the second plurality of thermocouple elements and the fourth plurality of thermocouple elements comprises an inner arc segment extending from an inner end of a tapered section and an outer arc segment extending from an outer end of the tapered section.

12. The sensor of claim 11, wherein the inner arc segments and the outer arc segments are concentric and subtend the same angle.

13. A differential scanning calorimeter comprising:
a measurement chamber comprising a thermopile sensor, wherein the thermopile sensor comprises:
a ceramic substrate;
a sample side thermopile comprising a first plurality of thermocouple elements of a first polarity and a second plurality of thermocouple elements of a second polarity, wherein segments of the thermocouple elements of the first polarity are diffusion-bonded to segments of the thermocouple elements of the second polarity to form thermocouple junctions;

a reference side thermopile comprising a third plurality of thermocouple elements of the first polarity and a fourth plurality of thermocouple elements of the second polarity, wherein segments of the thermocouple elements of the first polarity are diffusion-bonded to segments of the thermocouple elements of the second polarity to form thermocouple junctions;

a sample platform positioned and centered over the sample side thermopile; and a reference platform positioned and centered over the reference side thermopile, wherein:

the first plurality of thermocouple elements comprises outer arc segments that are diffusion bonded to the ceramic substrate and the third plurality of thermocouple elements comprises outer arc segments that are diffusion bonded to a ceramic substrate, the second plurality of thermocouple elements comprises inner arc segments that are diffusion bonded to the sample platform, and the fourth plurality of thermocouple elements comprises inner arc segments that are diffusion bonded to the reference platform, and the second polarity is opposite to the first polarity.

14. The differential scanning calorimeter of claim 13, further comprising heating and cooling means.

15. A sensor comprising:

a ceramic substrate comprising a hole;

the ceramic substrate comprising a raised flat surface surrounding the hole at its circumference;

a thermopile, positioned over the hole and supported on the raised flat surface, said thermopile comprising a plurality of positive thermocouple elements and a plurality of negative thermocouple elements, wherein segments of the positive thermocouple elements are diffusion bonded to segments of the negative thermocouple elements to form a plurality of diffusion bonded thermocouple junctions; and a platform centered over the thermopile, wherein the positive and negative thermocouple elements comprise outer arc segments that are diffusion bonded to the ceramic substrate, and wherein the positive and negative thermocouple elements comprise inner arc segments that are diffusion bonded to the platform.

16. The sensor of claim 15, wherein the plurality of thermocouple junctions are formed from thermocouple elements containing at least two of Pt, Pd and Au.

17. The sensor of claim 15, wherein the outer arc segments have inner edges, and wherein the inner edges of the outer arc segments are aligned with the circumference of the hole in the ceramic substrate.

18. The sensor of claim 15, wherein the outer arc segments comprise diffusion bonded thermocouple junctions that form a base region of the sensor.

19. The sensor of claim 15, wherein the inner arc segments comprise diffusion bonded thermocouple junctions that form a measurement region of the sensor.

20. The sensor of claim 15, wherein each of the positive and negative thermocouple elements of the thermopile has a Z shape, wherein the two ends of the Z are concentric arc segments subtending the same angle and connected by a tapered segment.

21. A twin thermopile sensor for a heat flux differential scanning calorimeter comprising:

a ceramic substrate having a sample position and a reference position;

a sample side thermopile centered on the sample position comprising a plurality of sample side thermocouple elements comprising a plurality of thermocouple elements of a first polarity and a plurality of thermocouple elements of a second polarity that are diffusion bonded to each other to form thermocouple junctions;

a reference side thermopile centered on the reference position comprising a plurality of reference side thermocouple elements comprising a plurality of thermocouple elements of the first polarity and a plurality of thermocouple elements of the second polarity that are diffusion bonded to each other to form thermocouple junctions;

a sample platform centered on the sample side thermopile and a reference platform centered on the reference side thermopile;

wherein the plurality of sample side thermocouple elements comprises outer arc segments that are diffusion bonded to the ceramic substrate, wherein the plurality of reference side thermocouple elements comprises outer arc segments that are diffusion bonded to the ceramic substrate, wherein the plurality of sample side thermocouple elements comprises inner arc segments that are diffusion bonded to the sample platform, and wherein the plurality of reference side thermocouple elements comprises inner arc segments that are diffusion bonded to the reference platform.

22. The twin thermopile sensor of claim 21, wherein the ceramic substrate is a disk supporting the sample thermopile and the reference thermopile.

23. The twin thermopile sensor of claim 22, wherein the outer and inner perimeters of the sample thermopile and the reference thermopile are circular.

24. The twin thermopile sensor of claim 21, wherein the outer arc segments and the inner arc segments are concentric and subtend the same angle.

25. The twin thermopile sensor of claim 21, wherein each of the thermocouple elements of the plurality of sample side thermocouple elements and the plurality of reference side thermocouple elements has a Z shape, with the outer arc segment connected to the inner arc segment by a tapered section.

26. The twin thermopile sensor of claim 21, wherein in the plurality of sample side thermocouple elements and in the plurality of reference side thermocouple elements the inner arc segments of the thermocouple elements of the second polarity overlap and are diffusion bonded to the inner arc segments of the thermocouple elements of the first polarity to form a measuring region thermocouple junction.

27. The twin thermopile sensor of claim 21, wherein in the plurality of sample side thermocouple elements and in the plurality of reference side thermocouple elements the outer arc segments of the thermocouple elements of the second polarity overlap and are diffusion bonded to the outer arc segments of the thermocouple elements of the first polarity to form a base region thermocouple junction.

28. The twin thermopile sensor of claim 21, wherein the outer perimeter of the sample side thermopile and the outer perimeter of the reference side thermopile form two adjacent circles of equal diameter.

* * * * *